(12) United States Patent
Oh et al.

(10) Patent No.: US 10,682,054 B2
(45) Date of Patent: Jun. 16, 2020

(54) APPARATUS FOR ANGIOGRAPHIC OPTICAL COHERENCE TOMOGRAPHY IN RETINA OR CHOROID, AND METHOD FOR DIAGNOSING DISEASES BY USING SAME

(71) Applicants: Korea Advanced Institute of Science and Technology, Daejeon (KR); Seoul National University Hospital, Seoul (KR)

(72) Inventors: Wangyuhl Oh, Daejeon (KR); Jang Ryul Park, Daejeon (KR); Kyuseok Kim, Seongnam-si (KR)

(73) Assignees: SEOUL NATIONAL UNIVERSITY HOSPITAL, Seoul (KR); KOREA ADVANCED INSTITUTE OF SCIENCE AND TECHNOLOGY, Dajeon (KR)

( * ) Notice: Subject to any disclaimer, the term of this patent is extended or adjusted under 35 U.S.C. 154(b) by 155 days.

(21) Appl. No.: 16/050,045

(22) Filed: Jul. 31, 2018

(65) Prior Publication Data
US 2018/0360307 A1   Dec. 20, 2018

Related U.S. Application Data

(63) Continuation of application No. PCT/KR2017/001088, filed on Feb. 1, 2017.

(30) Foreign Application Priority Data

Feb. 1, 2016   (KR) .................... 10-2016-0012442

(51) Int. Cl.
A61B 3/14      (2006.01)
A61B 3/10      (2006.01)
(Continued)

(52) U.S. Cl.
CPC ............ *A61B 3/102* (2013.01); *A61B 3/1241* (2013.01); *A61B 5/0066* (2013.01); *A61B 5/412* (2013.01);
(Continued)

(58) Field of Classification Search
CPC .................. A61B 3/102; A61B 5/0066; A61B 2090/3735; A61B 18/20
(Continued)

(56) References Cited

U.S. PATENT DOCUMENTS

2012/0287401 A1* 11/2012 Bizios .................. A61B 3/0025
351/206

FOREIGN PATENT DOCUMENTS

CN      103251383 A    8/2013
CN      103961058 A    8/2014
(Continued)

OTHER PUBLICATIONS

International Search Report dated Apr. 27, 2017.

*Primary Examiner* — Hung X Dang
(74) *Attorney, Agent, or Firm* — Dinsmore & Shohl LLP; Yongsok Choi, Esq.

(57) ABSTRACT

The present disclosure relates to an apparatus for angiographic optical coherence tomography in the retina or the choroid, and a method for diagnosing diseases by using the same and, more specifically, to: an apparatus for angiographic optical coherence tomography in the retina and the choroid, capable of diagnosing, at an early stage, shock states or diseases such as those of sepsis by quickly and objectively recognizing the low perfusion of tissue; and a diagnostic method using the same.

16 Claims, 9 Drawing Sheets

(51) Int. Cl.
*A61B 5/00* (2006.01)
*A61B 3/12* (2006.01)
*G01B 9/02* (2006.01)

(52) U.S. Cl.
CPC ........ *G01B 9/02091* (2013.01); *A61B 3/1233* (2013.01); *A61B 5/0035* (2013.01)

(58) Field of Classification Search
USPC ................................ 351/221, 246, 206, 220
See application file for complete search history.

(56) References Cited

FOREIGN PATENT DOCUMENTS

| | | | |
|---|---|---|---|
| JP | 2007-007398 | A | 1/2007 |
| JP | 2009-502220 | A | 1/2009 |
| JP | 2013-063215 | A | 4/2013 |
| KR | 10-2014-0015749 | A | 2/2014 |
| KR | 10-2014-0110498 | A | 9/2014 |

\* cited by examiner

APPARATUS FOR ANGIOGRAPHIC OPTICAL COHERENCE TOMOGRAPHY IN RETINA OR CHOROID, AND METHOD FOR DIAGNOSING DISEASES BY USING SAME

CROSS-REFERENCE TO RELATED APPLICATIONS

This application is a continuation of PCT/KR2017/001088 filed on Feb. 1, 2017, which claims priority to Korean Patent Application No. 10-2016-0012442 filed on Feb. 1, 2016, the entire contents of which are herein incorporated by reference.

FIELD OF THE INVENTION

The present disclosure relates to an apparatus for an angiographic optical coherence tomography in a retina or a choroid and a method for diagnosing diseases using the same, and more particularly, to an apparatus for an angiographic optical coherence tomography in a retina or a choroid, which is capable of diagnosing a shock state or a disease such as sepsis at an early stage by quickly and objectively recognizing the low perfusion of tissue, and a diagnosis method using the same.

BACKGROUND

Currently, diagnosis of sepsis and shock is comprehensively determined on the basis of clinical aspects, vital signs, a blood test, imaging examination, and the like.

The clinical aspects such as mental deterioration, a change in skin color, a reduction in urine volume, a capillary refill time, and the like are verified, and the vital signs such as a blood pressure, a heart rate, a breathing rate, a body temperature, and the like are observed. A blood leukocyte number, C-reactive protein (CRP), procalitonin, lactate, a liver somatic index, a kidney number, and the like are examined through the blood test, and bacteria, fungi, and the like are detected through a blood culture test. A lesion is verified by the imaging examination using plain roentgenography, computerized tomography (CT), magnetic resonance imaging (MRI), and the like.

Particularly, it is known that early diagnosis and treatment of sepsis and shock are very important. In fact, a mortality rate of patients who received antibiotics within one hour in sepsis was 19.5%, while a mortality rate of patients who did not receive antibiotics was 33.2%.

A related art is disclosed in Korean Patent Laid-Open Application No. 2005-0016987 (published on Feb. 21, 2005, entitled "Method for diagnosing sepsis using mitochondrial nucleic acid analysis"). However, the above-described conventional method is inevitably delayed in diagnosis.

Recently, in order to overcome such problems, techniques for diagnosing sepsis and shock through other methods have been developed.

A microcirculatory disorder is well known as major pathophysiology of sepsis and shock, and the microcirculatory disorder may be early detected even through other indexes such as a blood pressure and the like are normal.

When sepsis occurs, a blood flow rate of a body becomes relatively insufficient. Therefore, in order to maintain blood flow rates in important organs such as a heart, a brain, and the like, a self-protective mechanism acts to reduce blood flow rates in relatively less important organs such as skin, a gastrointestinal tract, muscles, and the like.

For this reason, a microcirculatory disorder is early detected compared with other indexes, and when the detected microcirculatory disorder is utilized, early diagnosis of sepsis and shock is possible, and in order for early diagnosis of sepsis and shock, there is also commercialization of health screening equipment so as to verify a microcirculatory disorder.

Typically, there are orthogonal polarization spectroscopy (OPS) and sidestream dark field (SDF) imaging. These equipment observe a microcirculatory change in a sublingual mucosa.

However, in the case of OPS and SDF imaging, a microcirculatory flow is measured at a sublingual mucosa, and there is a difference in the results depending on an observer in the microcirculatory flow measurement. OPS and SDF imaging perform a measurement by bringing an instrument into contact with a sublingual mucosa membrane, and thus the result depends on a force of the observer bring the instrument into contact with the sublingual mucosa membrane, and when the instrument is slightly strongly brought into contact with the sublingual mucosa membrane, capillaries are pressed and thus a blood flow is erroneously measured as not being present.

Therefore, there is a limit to objectively use OPS and SDF imaging, and thus it is necessary to develop a diagnostic technique capable of measuring a microcirculatory flow in a non-contact manner.

SUMMARY OF THE INVENTION

The present disclosure has been made in order to solve the above-described problems of the related art, and it is an object of the present disclosure to provide an apparatus for an angiographic optical coherence tomography in a retina or a choroid, which is capable of diagnosing a shock state or a disease such as sepsis at an early stage by non-invasively and non-contactly observing a low perfusion of tissue and quickly and objectively recognizing the low perfusion of tissue, and a diagnosis method using the same.

According to one aspect of the present disclosure, there is provided an apparatus 1 for an optical coherence tomography, which detects an optical coherence tomography signal with respect to an object, the apparatus 1 comprising a wavelength-swept laser 100 configured to emit an optical signal, a reference arm 200 having a path through which a part of the optical signal is transmitted through a coupler 110 and reflected by a reference mirror 210, a specimen arm 300 having a path through which a part of the optical signal is transmitted through the coupler 110, passes through a specimen scanner 310 configured to scan the object, and is reflected again by the specimen scanner 310, a detector 400 configured to detect an interference signal between the light reflected from the reference arm 200 and the light reflected from the specimen arm 300 using an interferometer for the optical signal, and a controller 500 configured to control a scan region and a scan interval for the object to be varied and scanned according to a predetermined rule in the specimen scanner 310 of the specimen arm 300 and collect interference information measured by the detector 400 to perform an image processing.

The object may be a retina or a choroid.

The specimen scanner 310 may comprise a collimator 311 configured to transmit light to a free space, a gavanometric mirror 312 for which the part of the optical signal emitted from the wavelength-swept laser 100 is incident via the collimator 311 and is reflected, and a scan optics configured with a plurality of lenses 313 for allowing the light reflected from the gavanometric mirror 312 to pass therethrough and reach the object.

The apparatus 1 may further comprise a high-speed data acquisition (DAQ) 600 provided between the detector 400 and the controller 500.

The reference arm 200 may further comprise a frequency shifter 230 configured to convert a frequency of the optical signal transmitted through the coupler.

According to another aspect of the present disclosure, there is provided a method for diagnosing a disease using the apparatus 1 for an optical coherence tomography, the method comprising a) a scanning operation of scanning, by a specimen scanner of the apparatus 1 for an optical coherence tomography, the object the number of times by varying a scan interval and a scan region, b) an image processing operation of merging and processing images obtained in the scanning operation, c) a repetitive scanning operation of repeatedly performing the scanning operation and the image processing operation at predetermined intervals, d) a reading operation of reading a microcirculatory change in a retina or a choroid through the obtained images, and e) a diagnosing operation of determining the presence or absence of a disease by comparing the result of the microcirculatory change obtained in the reading operation with a piece of reference data.

The scanning operation may comprise repeatedly scanning the same cross-sectional position of the retina or the choroid at various intervals.

More preferably, the object may be the choroid.

The scanning operation may comprise measuring a phase of an interference signal two or more times at regular intervals with respect to the same cross-sectional position of the retina or the choroid.

The scanning operation may comprise scanning both the retina and the choroid by varying a depth of a scan region.

The reading operation may comprise digitizing the images obtained through the repetitive scanning operation for each pixel and determining the presence or absence of a change in microcirculatory flow and a variation therein through a difference from a reference value.

Diagnosis or a treatment progress of the sepsis may be determined through a microcirculatory flow change in the retina or the choroid.

The sepsis may be diagnosed through the microcirculatory flow change in the choroid.

The method may further comprise, after the scanning operation is initially performed, performing the scanning operation one or more times within one hour to measure the microcirculatory flow change in the choroid and diagnose the sepsis.

The method may further comprise performing the scanning operation, the image processing operation, the repetitive scanning operation, and the reading operation two or more times within one hour.

Accordingly, the angiographic optical coherence tomography apparatus of the present disclosure and the diagnostic method using the same can diagnose a shock state or a disease such as sepsis at an early stage by quickly and objectively measuring a low perfusion of tissue.

In other words, in accordance with the present disclosure, when sepsis occurs, a retina or a choroid is non-invasively and non-contactly scanned and observed using a characteristic in which a microcirculatory disorder rapidly occurs in a low perfusion of tissue, and thus sampling of the retina or the choroid is not required, so that there is an advantage in that objectivity of a microcirculatory measurement can be increased and an immediate result analysis is possible.

Further, in accordance with the present disclosure, a microcirculatory disorder can be continuously observed as well as diagnosis of disease is possible, so that there is an advantage capable of being utilized as a treatment guide through a process of observing whether a microcirculatory flow improves.

DETAILED DESCRIPTION OF THE PREFERRED EMBODIMENTS

Hereinafter, an apparatus for angiographic optical coherence tomography in a retina or a choroid according to the present disclosure and a disease diagnosis method using the same will be described in detail with reference to the accompanying drawings.

The present disclosure relates to an apparatus 1 for an angiographic optical coherence tomography in a retina or choroid and a disease diagnosis method using the same and relates to a diagnosis technique capable of early diagnosing a disease by quickly and objectively recognizing a low perfusion in the retina or the choroid.

Figure 1:
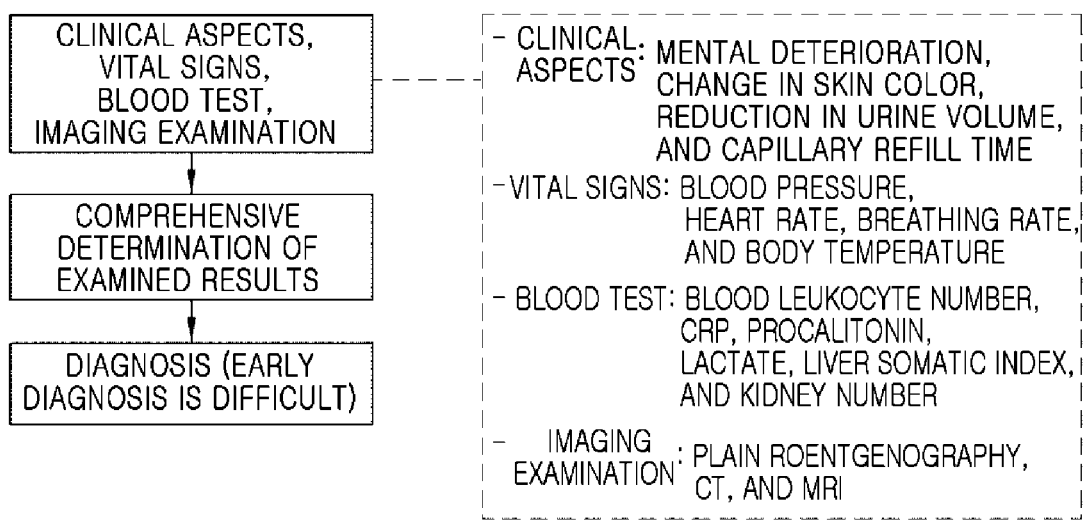
FIG. 1 is a flowchart illustrating a conventional process of early diagnosing a sepsis state.
Figure 2:
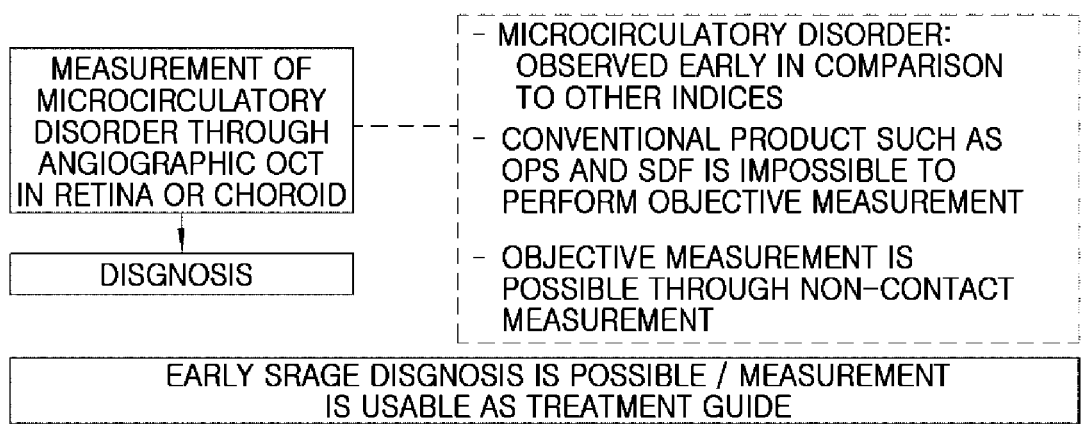
FIG. 2 is a flowchart schematically illustrating a disease diagnosis method using an optical coherence tomography apparatus according to the present disclosure.
Figure 3:
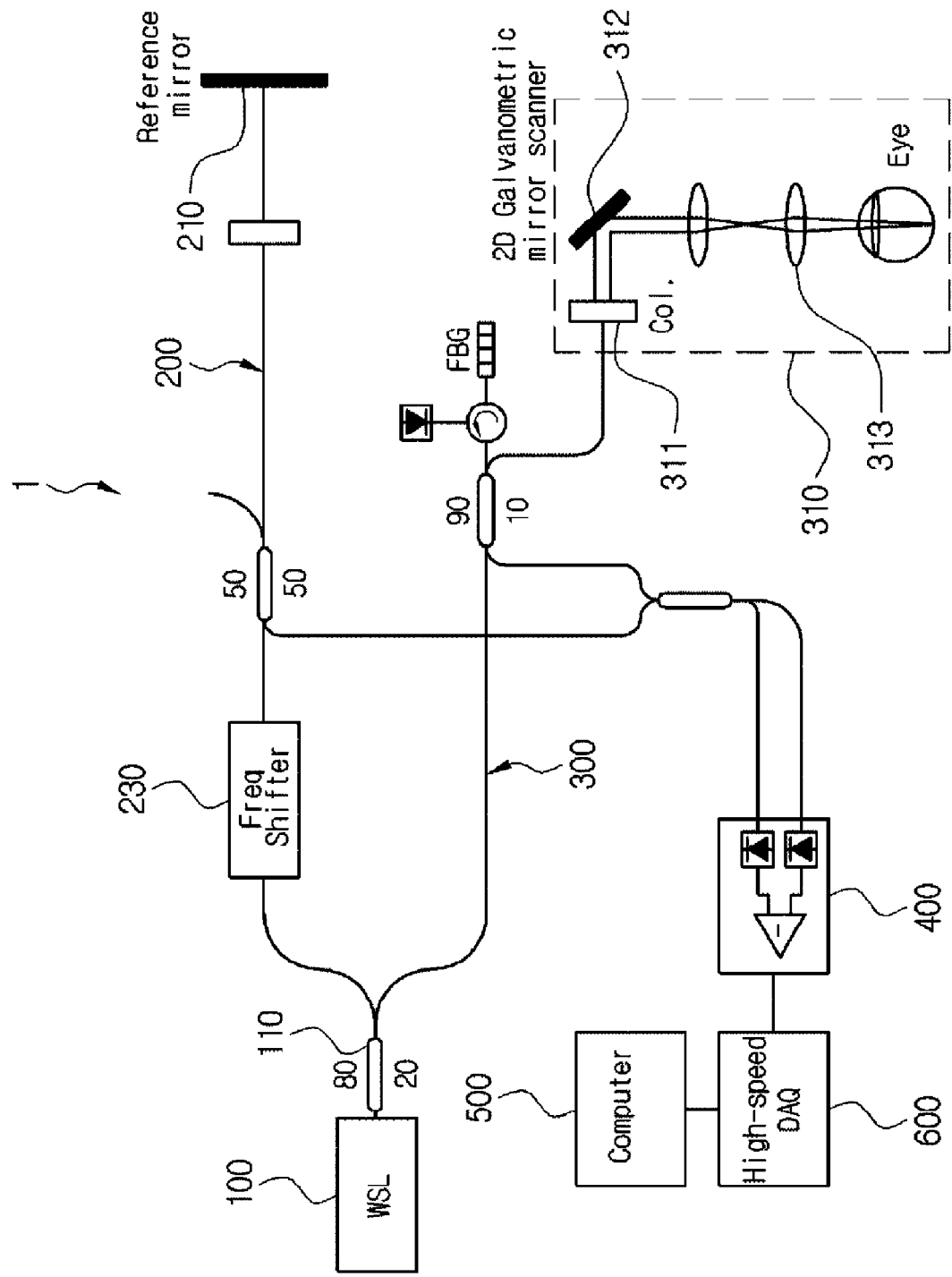
FIG. 3 is a schematic diagram of the optical coherence tomography apparatus according to the present disclosure.

As shown in FIG. 3, the apparatus 1 for an optical coherence tomography according to the present disclosure detects an optical coherence tomography signal for a retina or a choroid and comprises a wavelength-swept laser 100, a reference arm 200, a specimen arm 300, a detector 400, and a controller 500.

In the present disclosure, the wavelength-swept laser 100 emits an optical signal to an object, i.e., a specimen scanner 310 for observing a retina or a choroid of an eyeball, and the wavelength-swept laser 100 is configured with an amplification medium for emitting and amplifying light, and a variable filter capable of converting a pass band according to a time.

The reference arm 200 has a path through which a part of an optical signal emitted from the wavelength-swept laser 100 is transmitted through a coupler and then is reflected by a reference mirror 210, and the specimen arm 300 has a path through which the remaining optical signal, which is not transmitted to the reference arm 200, is transmitted to the specimen scanner 310 configured to scan a retina or a choroid and then is reflected.

A frequency shifter 230 configured to convert a frequency of the optical signal transmitted through the coupler may further be provided at the reference arm 200.

At this point, the specimen scanner 310 may be configured with a collimator 311 configured to transmit light to a free space, a gavanometric mirror 312 configured to reflect a part of the optical signal being incident via the collimator 311 after being emitted from the wavelength-swept laser 100, and a plurality of lenses 313 through which the light reflected from the gavanometric mirror 312 passes to reach a retina or a choroid.

Accordingly, in the specimen scanner 310, light emitted from the wavelength-swept laser 100 and passing through the collimator 311 is reflected by the gavanometric mirror 312, and the reflected light reaches the retina or choroid via the plurality of lenses 313 serving as scan optics and is reflected therefrom.

That is, in the present disclosure, an eyeball of human is disposed in the scan optics to be used as the objective lens 313, so that the choroid which is a rear portion of the retina can be observed.

As described above, the light reflected from the retina or choroid reaches the detector 400, and the detector 400 detects an interference signal between the lights reflected from the reference arm 200 using an interferometer for the optical signals.

The controller 500 controls a scan region and a scan interval for the retina or choroid to be varied and scanned according to a predetermined rule in the specimen scanner 310 of the specimen arm 300, and collects interference information measured by the detector 400 and performs an image processing.

In this case, the controller 500 may be a central processing unit (CPU) or a microprocessor, and the controller 500 may collect the interference information measured by the detector 400 through a high-speed data acquisition (DAQ) 600 and may generate an image through an image processing.

Describing an operation of the apparatus 1 for an optical coherence tomography of FIG. 3 briefly, the apparatus 1 for an optical coherence tomography of the present disclosure is configured in the form of a Michelson interferometer in which a wavelength swept laser (WSL) of which wavelength is varied according to a time is used as a light source, and light emitted from the wavelength-swept laser 100 is first divided into 20:80 through a coupler in two paths of the reference arm 200 and the specimen arm 300.

The light reciprocating through the reference arm 200 has frequency values greater than zero through the frequency shifter 230, and thus a measurable depth of an imaging device is improved.

Light backward scattered and returned from the specimen (eyeball) and light reflected from the reference mirror 210 are combined at a 50:50 optocoupler to generate an interference signal, and then the generated interference signal is converted into a digital signal through the detector 400 and the DAQ 600. The interference signal is converted into three-dimensional (3D) vascular information and blood flow information by a post-processing.

Next, a method for diagnosing a disease using the apparatus 1 for an optical coherence tomography according to the present disclosure may comprise a) a scanning operation of scanning, by the specimen scanner of the apparatus 1 for an optical coherence tomography, a retina or a choroid of human the number of times by varying a scan interval and a scan region, b) an image processing operation of merging and processing images obtained in the scanning operation, c) a repetitive scanning operation of repeatedly performing the scanning operation and the image processing operation at predetermined intervals, d) a reading operation of reading a microcirculatory change in the retina or choroid through the obtained images, and e) a diagnosing operation of comparing the result of the microcirculatory change obtained in the reading operation with a piece of reference data to determine the presence or absence of a disease.

Figure 4:
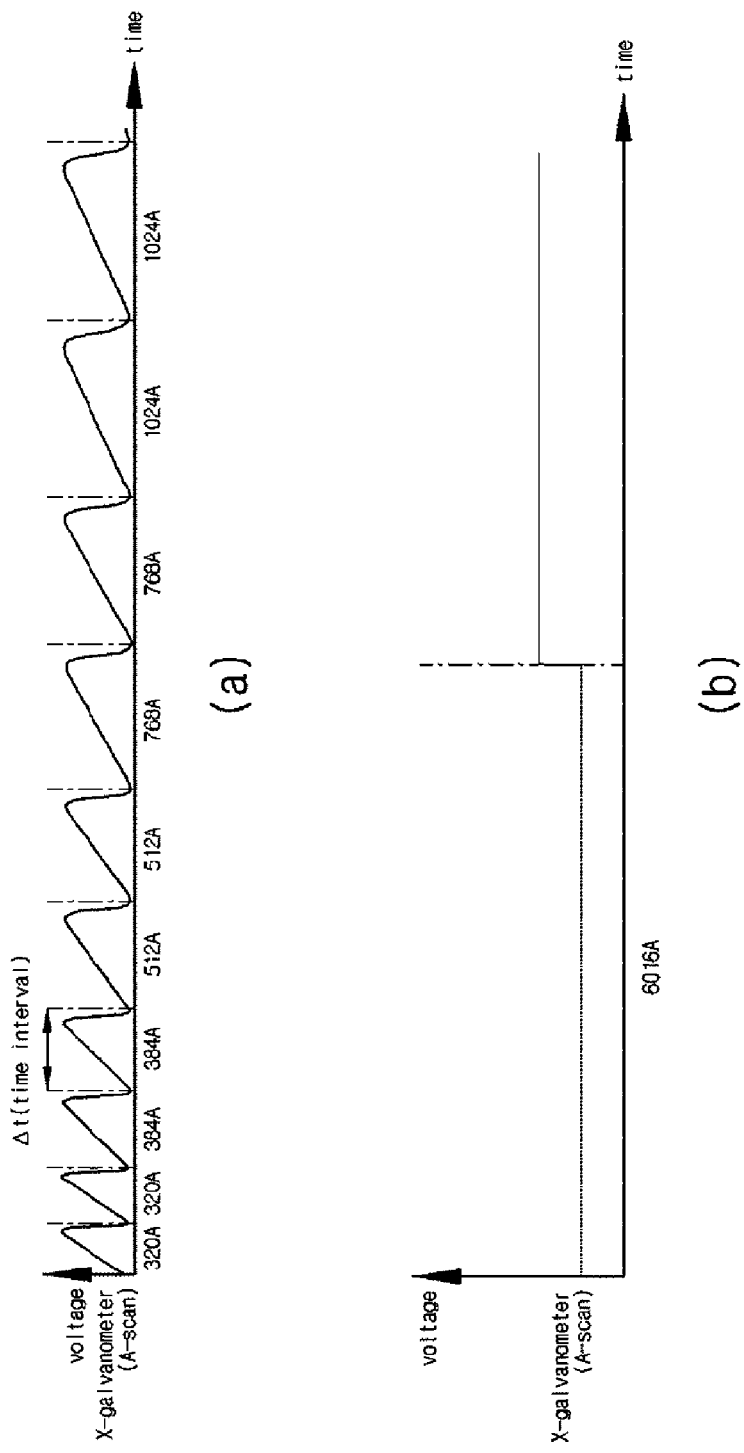
FIG. 4 is graphs showing an example of an imaging operation in a disease diagnosis method using the optical coherence tomography apparatus according to the present disclosure.

As described above, the scanning operation comprises repeatedly scanning by varying a scan interval and a scan region the retina or choroid, and FIG. 4 illustrates an example of a method for repeatedly scanning the same cross-sectional position of the specimen (eyeball) at various intervals so as to measure a blood flow speed.

As shown in FIG. 4(a), in order to calculate a blood flow speed using the apparatus 1 for an optical coherence tomography, the scanning operation comprises measuring a phase change value according to a time by measuring a phase of the interference signal at least two times with respect to the same spatial position of the specimen at a predetermined time interval.

When this direction is defined as z, a fast axis beam scan direction is defined as x, and a slow axis beam scan direction is defined as y, FIG. 4(a) illustrates an example of scanning in the x direction and FIG. 4(b) illustrates an example of scanning in the y direction.

When the wavelength-swept laser (WSL) 100 sweeps once, a single A-line in a depth direction is obtained, and when fast axis beam scans (x scan) are sequentially performed at regular intervals, a single image may be obtained.

At this point, when the same position is continuously scanned, a time interval is equal to the number of scanned A-lines.

It can be seen from FIG. 4(a) that, when a time required for imaging a single A-line is A, the number of A-lines is 320, and when a repetitive scanning is performed, a time interval between x scans is 320A. With this principle, when the scanning is performed twice with 320, 384, 512, 768, and 1024, it is possible to obtain information in which the time interval between the same x scanning is 320A, 384A, 512A, 768A, and 1024A. After one set of the x scanning is completed, a position of the y scanning is shifted upward immediately, and then the above-described scanning is repeated.

Figure 5:
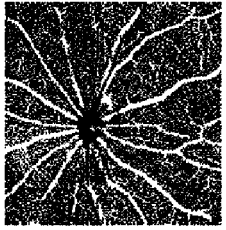
FIG. 5 is microcirculatory images of a retina and a choroid, which are taken while a scan interval is changed using the optical coherence tomography apparatus of the present disclosure.

FIG. 5 shows images of the retina and choroid, which are obtained through the above-described process, and a leftmost image of FIG. 5 is obtained when the scan interval is shortened and the scan interval is gradually increased toward a right side.

Eyes are one of the most important organs connected to a brain, and a body recognizes the retina of the eyes as the same important organ as blood vessels in the brain, while the body recognizes a choroid layer as an organ that is less important than the retina.

Consequently, when sepsis occurs as shown in FIG. 5, it can be seen that a change in blood flow of the retina hardly occurs at an initial stage, and a change in blood flow of the choroid occurs more rapidly.

At this point, when the scan interval is set too fast, since a microcirculatory flow of the choroid in which a blood flow speed becomes slower is not measured, it is necessary to set the scan interval to a predetermined interval or more.

Figure 6:
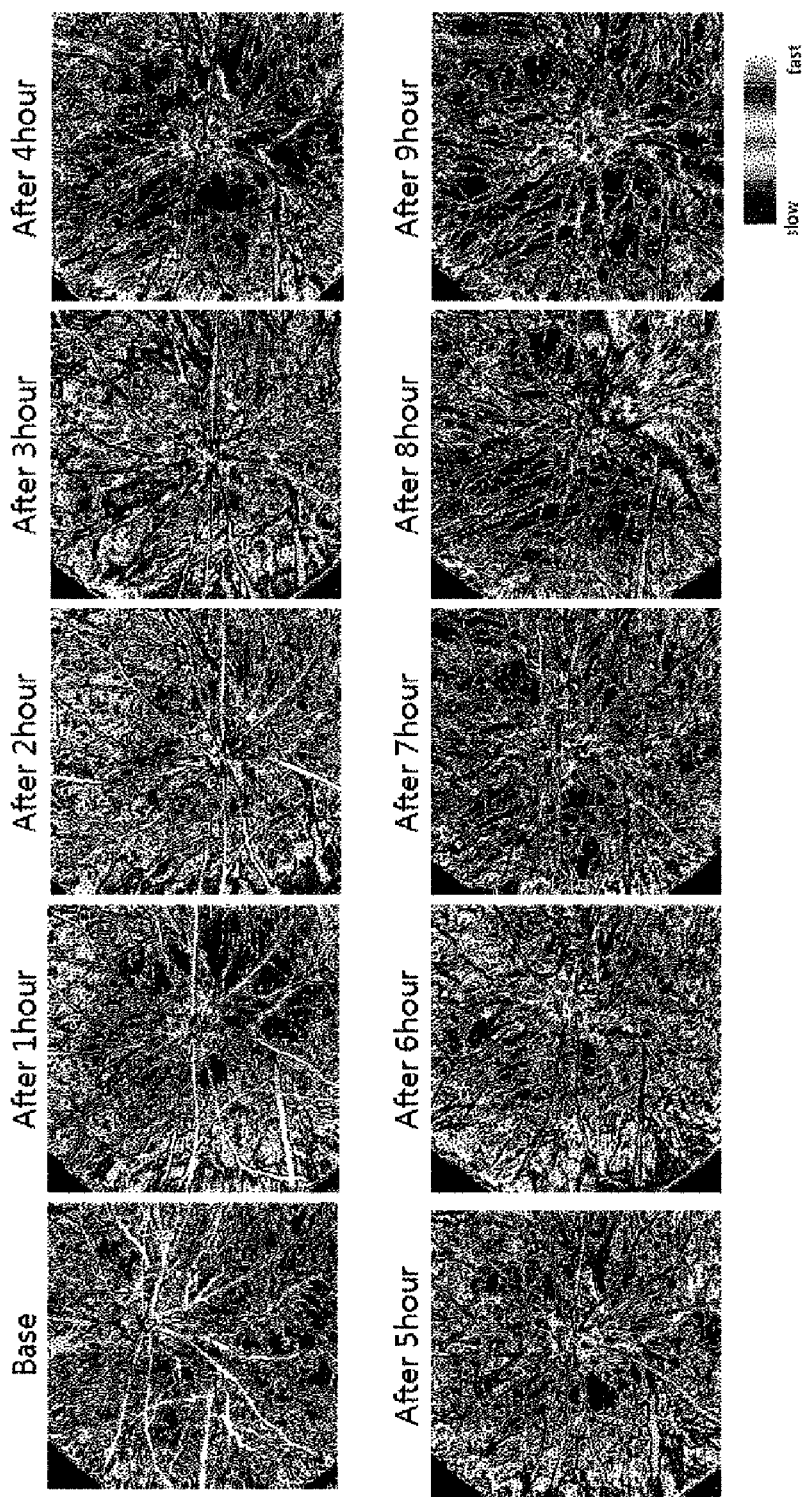
FIG. 6 is images of a microcirculatory flow of a choroid, which are taken at one hour intervals using the optical coherence tomography apparatus of the present disclosure.

FIG. 6 shows images of the choroid scanned at one hour intervals for nine hours in consideration of characteristics of vital signs that a microcirculatory disorder generally occurs after approximately one hour from a point of time when after sepsis occurs, lactate increases after four hours, and a blood pressure decreases after six hours.

As shown in FIG. 6, in the present disclosure, it can be visually confirmed that reduction in microcirculatory flow speed occurs in the choroid after approximately one hour through the images scanned by the apparatus 1 of an optical coherence tomography.

That is, a phenomenon in which a blood flow rate decreases abruptly occurs in the choroid after approximately one hour from a point of time when the sepsis occurs, and after that, a tendency in which the blood flow rate decreases steadily is observed, but a significant change does not occur in the retina layer compared with the choroid from the point of time when the sepsis occurs.

Accordingly, in the present disclosure, the choroid which rapidly changes after the occurrence of sepsis is scanned using the apparatus 1 for an optical coherence tomography, and the result is used for the diagnosis of sepsis.

Then, the reading operation comprises digitizing the image files obtained through the repetitive scanning operation for each pixel and determining the presence or absence of a change in microcirculatory flow and a variation therein through a difference from a reference value.

Figure 7:
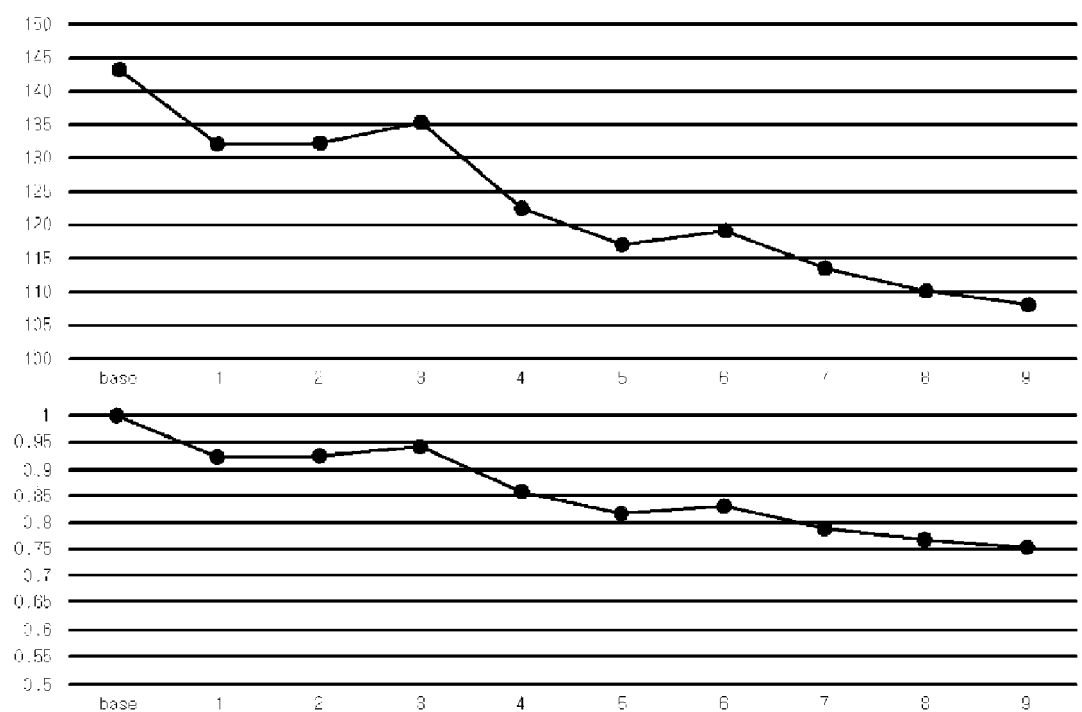
FIG. 7 is a graph showing changes over time by converting the images in FIG. 6 into a color scale of a bmp image for each pixel and then performing a predetermined calculation.
Figure 8:
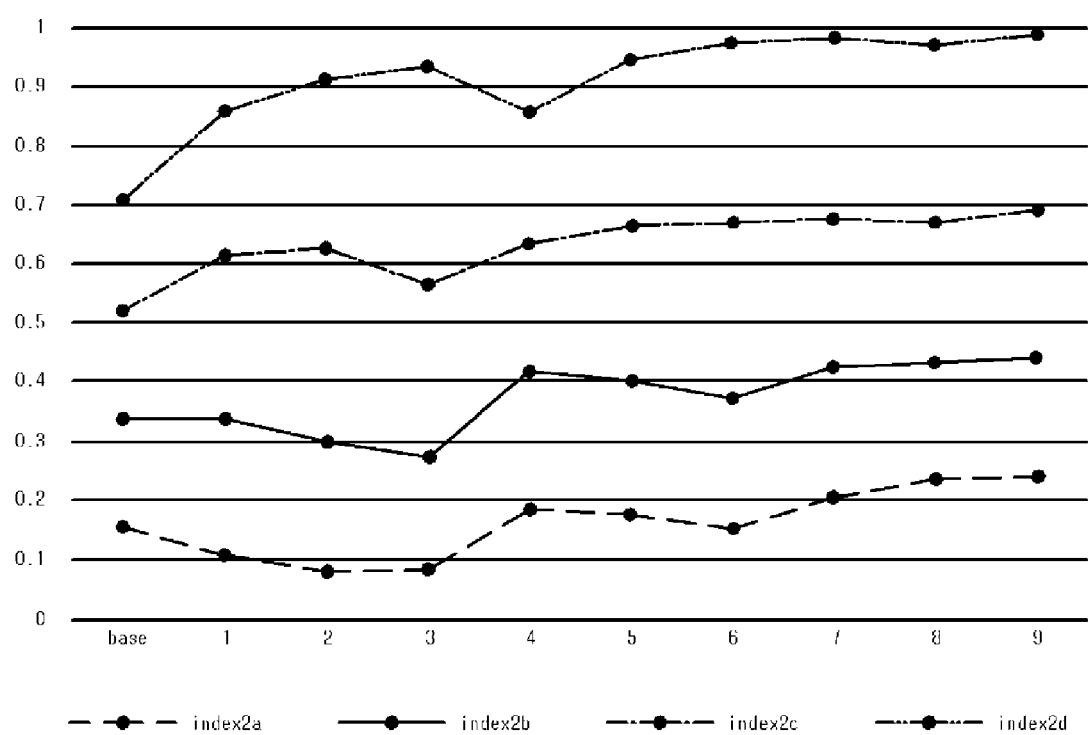
FIG. 8 is a graph showing changes over time by converting the images in FIG. 6 into a color scale of a bmp image for each pixel and then performing a predetermined calculation.
Figure 9:
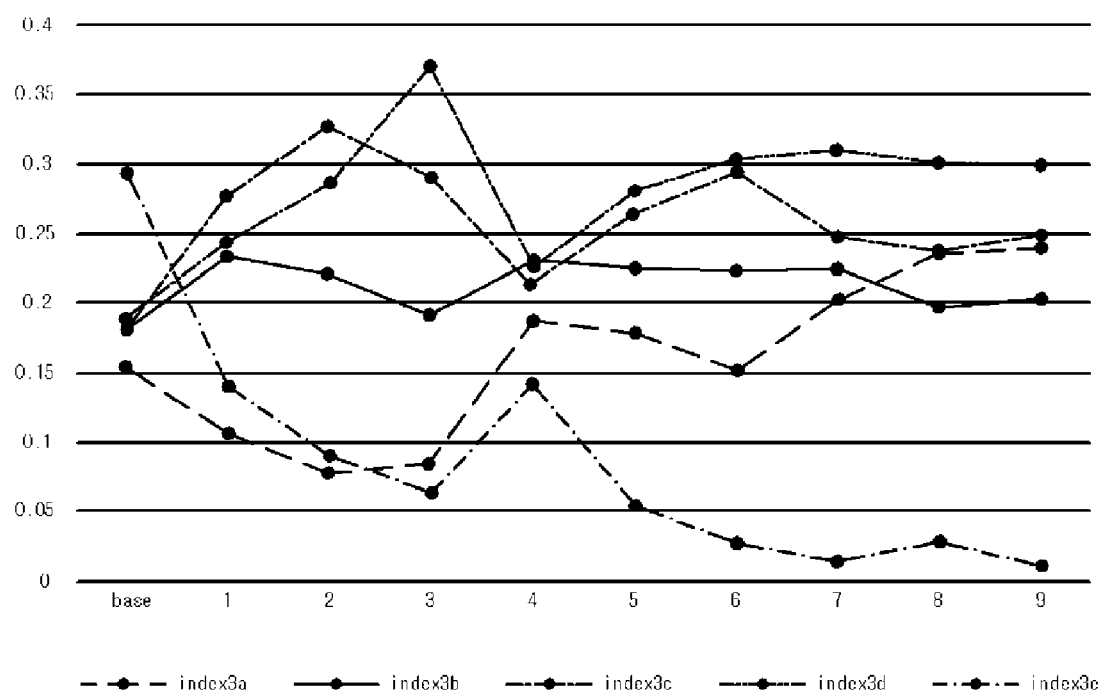
FIG. 9 is a graph showing changes over time by converting the images in FIG. 6 into a color scale of a bmp image for each pixel and then performing a predetermined calculation.

FIGS. 7 to 9 show graphs showing changes over time by converting the scanned images into a color scale of a bmp image for each pixel and then performing a predetermined calculation, and through the graphs, it is confirmed that large numerical changes occur in the images after one hour.

FIG. 7 illustrates a graph obtained by converting images having the same size with respect to the same region into color scale values for each pixel using a characteristic of a bmp image having a color scale in the range of 0 to 255 and then calculating and displaying a value by dividing the sum of the color scale values for each pixel by a total number of pixels. At this point, an x-axis indicates a time, and a y-axis indicates the calculated value as described above.

Next, FIGS. 8 and 9 show a total ratio (0 to 1) of pixels having a color scale value in the range of x to y, and in FIG. 8, an index 2a indicates 1 to (255*0.2), an index 2b indicates 1 to (255*0.4), an index 2c indicates 1 to (255*0.6), and an index 2d indicates 1 to (255*0.8), and an area under each graph represents an amount of blood vessels scanned per interval.

In FIG. 9, an index 3a indicates 1 to (255*0.2), an index 3b indicates (255*0.2) to (255*0.4), an index 3c indicates (255*0.4) to (255*0.6), an index 3d indicates (255*0.6) to (255*0.8), and an index 3e indicates (255*0.8) to (255*1.0), and sections corresponding to 0 to 20%, 20 to 40%, 40 to 60%, 60 to 80%, and 80 to 100% are discriminately displayed.

Accordingly, in the diagnosing operation, the presence or absence of the disease may be determined by comparing the read result with respect to the digitized images with a piece of reference data, i.e., a piece of data of a normal person.

In other words, the disease diagnosis method of the present disclosure may determine the presence or absence of disease through only visual observation of the images obtained in the image processing operation, but the disease diagnosis method of the present disclosure may compare the digitized images with the piece of reference data, thereby objectively determining the presence or absence of disease as well as the progress of disease through a difference value obtained by the comparison.

In summary, according to the disease diagnosis method of the present disclosure, when an apparatus for an angiographic optical coherence tomography (OCT) scans, the same cross-sectional position of a blood vessel is repeatedly scanned at various intervals, and a phase of an interference signal is measured twice or more at regular intervals with respect to the same cross-sectional position. Then, in the present disclosure, the image files obtained through the repetitive scanning operation are digitized for each pixel, and the presence or absence of a change in microcirculatory flow and a variation therein are determined through a difference from the reference value.

Accordingly, the apparatus 1 for an angiographic OCT of the present disclosure and the diagnostic method using the same can diagnose a disease or a shock state such as sepsis at an early stage by quickly and objectively measuring a low perfusion of tissue.

Further, in accordance with the present disclosure, a microcirculatory disorder can be continuously observed as well as diagnosis of disease is possible, thereby being utilized as a treatment guide through a process of observing whether a microcirculatory flow improves. The present disclosure is not limited to the above-described embodiments and is applicable to various application ranges, and it will be apparent that various modifications can be devised by those skilled in the art to which the present disclosure pertains without departing from the gist of the present disclosure as defined by the appended claims.

What is claimed is:

1. An apparatus for an optical coherence tomography, which detects an optical coherence tomography signal with respect to an object, the apparatus comprising:
   a wavelength-swept laser configured to emit an optical signal;
   a reference arm having a path through which a part of the optical signal is transmitted through a coupler and reflected by a reference mirror;
   a specimen arm having a path through which a part of the optical signal is transmitted through the coupler, passes through a specimen scanner configured to scan the object, and is reflected again from the object;
   a detector configured to detect an interference signal between light reflected from the reference arm and light reflected from the specimen arm using an interferometer for the optical signal; and
   a controller configured to control a scan region and a scan interval for the object to be varied and scanned according to a predetermined rule in the specimen scanner of the specimen arm and collect interference information measured by the detector to perform an image processing.

2. The apparatus of claim 1, wherein the object is a retina or a choroid.

3. The apparatus of claim 1, wherein the specimen scanner comprises:
   a collimator configured to transmit light to a free space;

a gavanometric mirror for which a part of the optical signal emitted from the wavelength-swept laser is incident via the collimator and is reflected; and a scan optics configured with a plurality of lenses for allowing the light reflected from the gavanometric mirror to pass through the plurality of lenses and reach the object.

4. The apparatus of claim 1, further comprising:
a high-speed data acquisition (DAQ) provided between the detector and the controller.

5. The apparatus of claim 1, wherein the reference arm further comprises a frequency shifter configured to convert a frequency of the optical signal transmitted through the coupler.

6. A method for diagnosing a disease using the apparatus of claim 1, the method comprising:
 a) a scanning operation of scanning, by a specimen scanner of the apparatus for an optical coherence tomography, the object the number of times by varying a scan interval and a scan region;
 b) an image processing operation of merging and processing images obtained in the scanning operation;
 c) a repetitive scanning operation of repeatedly performing the scanning operation and the image processing operation at predetermined intervals;
 d) a reading operation of reading a microcirculatory change in a retina or a choroid through the obtained images; and
 e) a diagnosing operation of determining the presence or absence of a disease by comparing the result of the microcirculatory change obtained in the reading operation with a piece of reference data.

7. The method of claim 6, wherein the object is a retina or a choroid.

8. The method of claim 7, wherein the object is the choroid.

9. The method of claim 7, wherein the scanning operation comprises repeatedly scanning the same cross-sectional position of the retina or the choroid at various intervals.

10. The method of claim 9, wherein the scanning operation comprises measuring a phase of an interference signal two or more times at regular intervals with respect to the same cross-sectional position of the retina or the choroid.

11. The method of claim 10, wherein the scanning operation comprises scanning both the retina and the choroid by varying a depth of a scan region.

12. The method of claim 7, wherein diagnosis or a treatment progress of sepsis is determined based on a microcirculatory flow change in the retina or the choroid.

13. The method of claim 12, wherein the sepsis is diagnosed based on the microcirculatory flow change in the choroid.

14. The method of claim 13, further comprising:
after the scanning operation is initially performed, performing the scanning operation one or more times within one hour to measure the microcirculatory flow change in the choroid and diagnose the sepsis.

15. The method of claim 6, wherein the reading operation comprises digitizing the images obtained by the repetitive scanning operation for each pixel and determining the presence or absence of a change in microcirculatory flow and a variation therein through a difference from a reference value.

16. The method of claim 6, further comprising:
performing the scanning operation, the image processing operation, the repetitive scanning operation, and the reading operation twice or more times within one hour.

* * * * *